United States Patent
Usui et al.

(10) Patent No.: US 10,877,165 B2
(45) Date of Patent: Dec. 29, 2020

(54) DOSIMETER CONTAINER AND DOSAGE MEASURING BODY

(71) Applicant: Nippon Light Metal Company, Ltd., Tokyo (JP)

(72) Inventors: Hideaki Usui, Tokyo (JP); Hidaka Furuya, Aichi (JP); Maki Takahashi, Tokyo (JP); Hidenori Ishikawa, Tokyo (JP)

(73) Assignee: Nippon Light Metal Company, Ltd., Tokyo (JP)

( * ) Notice: Subject to any disclaimer, the term of this patent is extended or adjusted under 35 U.S.C. 154(b) by 0 days.

(21) Appl. No.: 15/777,164

(22) PCT Filed: Mar. 27, 2018

(86) PCT No.: PCT/JP2018/012576
§ 371 (c)(1),
(2) Date: May 17, 2018

(87) PCT Pub. No.: WO2018/181395
PCT Pub. Date: Oct. 4, 2018

(65) Prior Publication Data
US 2020/0124743 A1    Apr. 23, 2020

(30) Foreign Application Priority Data
Mar. 31, 2017 (WO) ................ PCT/JP2017/013684

(51) Int. Cl.
*G01T 1/02* (2006.01)
*A61N 5/10* (2006.01)
(Continued)

(52) U.S. Cl.
CPC ............ *G01T 1/02* (2013.01); *A61N 5/10* (2013.01); *G01T 7/02* (2013.01); *G21F 3/00* (2013.01); *G21F 5/06* (2013.01); *A61N 2005/109* (2013.01)

(58) Field of Classification Search
CPC .... G01T 1/02; G01T 7/02; A61N 5/10; A61N 2005/109; G21F 3/00; G21F 5/06
See application file for complete search history.

(56) References Cited

U.S. PATENT DOCUMENTS 3,426,197 A    2/1969 Waly et al.
4,171,485 A    10/1979 Marshall
(Continued)

FOREIGN PATENT DOCUMENTS

DE    10 2011 054 846 B3    2/2013
JP    S51-094098    8/1976
(Continued)

OTHER PUBLICATIONS

Notification of Reasons for Refusal issued in the JP Patent Application No. 2018-517656, dated Dec. 18, 2018.
(Continued)

*Primary Examiner* — Michael C Miggins
(74) *Attorney, Agent, or Firm* — Knobbe Martens Olson & Bear, LLP

(57) ABSTRACT

A dosimeter container comprising a housing portion and a shield portion that surrounds the housing portion is provided. The housing portion houses a radiation dosage measuring device for measuring a dosage of predetermined radiation other than neutron radiation. The shield portion is composed of a member made of a material that transmits predetermined radiation and shields neutron radiation. The shield portion is a LiF sintered body, in particular, a $^6$LiF sintered body. Further, the shield portion includes at least (Continued)

PERSPECTIVE VIEW OF DOSIMETER CONTAINER 10 two or more shield portion components (a body portion and a lid portion), in which adjacent members can abutt against each other. The housing portion is same size as or larger than the size of the radiation dosage measuring device; and the housing portion extends over the entirety of the components. The dosimeter container is preferably used as a dosage measuring body having a radiation dosage measuring device stored in the housing portion.

7 Claims, 14 Drawing Sheets

(51) Int. Cl.
    *G01T 7/02* (2006.01)
    *G21F 3/00* (2006.01)
    *G21F 5/06* (2006.01)

(56) References Cited

U.S. PATENT DOCUMENTS

| | | |
|---|---|---|
| 4,346,511 A | 8/1982 | Jones et al. |
| 2011/0186720 A1 | 8/2011 | Jongen et al. |
| 2011/0284731 A1 | 11/2011 | Roscoe et al. |
| 2014/0332678 A1 | 11/2014 | Tkabladze et al. |
| 2017/0108591 A1 | 4/2017 | Kuri et al. |
| 2018/0001112 A1 | 1/2018 | Liu et al. |

FOREIGN PATENT DOCUMENTS

| | | |
|---|---|---|
| JP | S54-018289 U | 2/1979 |
| JP | H08-201581 | 8/1996 |
| JP | 2001-294853 | 10/2001 |
| JP | 2011-526504 A | 10/2011 |
| JP | 2016-003892 | 1/2016 |
| SU | 1144503 A1 | 8/1985 |
| WO | WO 2016/177270 A1 | 11/2016 |

OTHER PUBLICATIONS

Partial Supplementary European Search Report issued in the EP Patent Application No. EP18729857.5, dated Feb. 1, 2019.
Notification of Reasons for Refusal issued in the JP Patent Application No. 2018-517656, dated Jan. 14, 2020.
Extended European Search Report received in EP Application No. 18729857.5, dated Apr. 10, 2019.
Office Action received in Russian Patent Application No. 2018123313, dated Apr. 9, 2019.

PERSPECTIVE VIEW OF
DOSIMETER CONTAINER 10

FRONT VIEW OF
DOSIMETER CONTAINER 10

CROSS-SECTIONAL VIEW
AT A-A SECTION OF FIG. 1B

PERSPECTIVE VIEW OF
BODY PORTION 12A

PERSPECTIVE VIEW OF
LID PORTION 12B

PERSPECTIVE VIEW OF
DOSAGE MEASURING BODY 1

PERSPECTIVE VIEW OF
DOSIMETER CONTAINER 20

FRONT VIEW OF
DOSIMETER CONTAINER 20

CROSS-SECTIONAL VIEW
AT A-A SECTION OF FIG. 2B

PERSPECTIVE VIEW OF
BODY PORTION 22A

PERSPECTIVE VIEW OF
LID PORTION 22B

PERSPECTIVE VIEW OF
DOSAGE MEASURING BODY 2

PERSPECTIVE VIEW OF
DOSIMETER CONTAINER 30

FRONT VIEW OF
DOSIMETER CONTAINER 30

TOP VIEW OF
DOSIMETER CONTAINER 30

CROSS-SECTIONAL VIEW
AT A-A SECTION OF FIG. 3C

PERSPECTIVE VIEW OF
BODY PORTION 32A

PERSPECTIVE VIEW OF
LID PORTION 32B

PERSPECTIVE VIEW OF
DOSAGE MEASURING BODY 3

PERSPECTIVE VIEW OF
DOSIMETER CONTAINER 40

FRONT VIEW OF
DOSIMETER CONTAINER 40

TOP VIEW OF
DOSIMETER CONTAINER 40

CROSS-SECTIONAL VIEW
AT A-A SECTION OF FIG. 4C

PERSPECTIVE VIEW OF
BODY PORTION 42A

PERSPECTIVE VIEW OF
LID PORTION 42B

PERSPECTIVE VIEW OF
DOSAGE MEASURING BODY 4

DOSIMETER CONTAINER AND DOSAGE MEASURING BODY

This application is the U.S. National Phase under 35 U.S.C. § 371 of International Application No. PCT/JP2018/012576, filed Mar. 27, 2018, designating the U.S., which claims priority to International Application No. PCT/JP2017/013684, filed Mar. 31, 2017, the entire contents of which are incorporated herein by reference.

TECHNICAL FIELD

The present invention relates to a dosimeter container and a dosage measuring body for measuring a dosage of radiation other than neutron radiation, such as gamma radiation.

BACKGROUND ART

In recent years, Boron Neutron Capture Therapy (BNCT) has been under extensive research and development as a rapidly emerging therapy for cancer. Boron Neutron Capture Therapy represents a radiotherapy that uses neutron radiation. First, a boron compound designed to be specifically incorporated into cancer cells is administered to a patient. Then, cancer cells in which the boron compound has been accumulated are irradiated with neutron radiation controlled to have an energy within a predetermined range. A collision of the neutron radiation with the boron compound will generate an α ray. That α ray will kill the cancer cells.

Boron Neutron Capture Therapy is a promising method of treating cancer, and is on the verge of advancing to the clinical trial stage. A neutron radiation irradiation apparatus used for Boron Neutron Capture Therapy is designed to achieve a therapeutic effect by taking advantage of radiation such as thermal neutron radiation and epithermal neutron radiation. A neutron radiation irradiation environment may be viewed as a field where types of radiation having energies within a certain range coexist. Considering the above view of the neutron radiation irradiation environment, required is a step of selectively measuring only gamma radiation as isolated as possible to ensure the safety of the apparatus and other factors.

To date, a neutron radiation generator for use in the neutron radiation irradiation apparatus has always been a nuclear reactor. However, in recent years, a small neutron generator for in-hospital use has been emerging. The small neutron generator is configured to allow protons and deuterons accelerated in an accelerator to collide against a target of beryllium or lithium. The resulting neutron radiation, which includes a higher proportion of thermal and epithermal neutrons as compared with those generated by a conventional generator, is decelerated with a moderator to provide a neutron radiation irradiation environment having less negative effects on the human body.

In a neutron radiation irradiation environment, there coexist types of radiation having effects on the human body such as gamma radiation, including gamma radiation radioactivated by irradiation with neutron radiation, in addition to neutron radiation. When gamma radiation is measured in the presence of neutron radiation, the dosage of gamma radiation may not be accurately determined due to the influence of the neutron radiation even when a dedicated dosimeter is used for detection.

As an approach for enhancing the measurement accuracy of a dosage of gamma radiation, a gamma radiation measuring device has been proposed, the gamma radiation measuring device including a first detector, the first detector including a filter, the filter being arranged around a radiation dosimeter of the same type as a radiation dosimeter constituting a second detector to be used together, and being made of lead or a lead alloy and having a thickness such that the decay of neutrons and the correction coefficient of gamma radiation fall within an acceptable range for measuring gamma radiation (see Patent Document 1).

However, lead blocks gamma radiation, but not neutron radiation. Further, lead and lead alloys themselves may emit gamma radiation due to radioactivation when exposed to neutron radiation. Therefore, the dosage of gamma radiation needs to be calculated from the difference between a detection result from a radiation detector provided in the inside of a filter made of lead or a lead alloy and a detection result from a radiation detector provided outside of the filter. Consequently, the approach described in Patent Document 1 may result in complicated procedures as well as a radiation dosimeter that is larger in size.

Moreover, in view of demands for a neutron-radiation shielding material, a shape-formable composition for forming radiation protection equipment has been proposed, in which a radiation shielding material such as lithium fluoride is kneaded with a thermoplastic resin having a melting point of 40 to 80° C. (see Patent Document 2).

However, in the shape-formable composition described in Patent Document 2, a limited range of the ratio of a radiation shielding material such as a lithium compound which can be mixed with a resin requires a shielding material having a larger thickness in order to obtain a sufficient shielding effect. Moreover, a resin component may be slightly radioactivated to emit gamma radiation when irradiated with neutron radiation. This may affect measurement results from a dosimeter.

Patent Document 1: Japanese Unexamined Patent Application, Publication No. 2016-3892

Patent Document 2: Japanese Unexamined Patent Application, Publication No. H08-201581

DISCLOSURE OF THE INVENTION

Problems to be Solved by the Invention

The present invention is made in view of the aforementioned actual circumstances. An object of the present invention is to provide a dosimeter container which contributes to both an improvement in measurement accuracy of a radiation dosage and a downsizing of a measuring apparatus.

Means for Solving the Problems

The present inventors conducted extensive studies to achieve the above object. As a result, the present inventors have found that a dosimeter container which contributes to both an improvement in measurement accuracy of a radiation dosage and a downsizing of a measuring apparatus can be obtained when the dosimeter container includes: a housing portion for housing a specific radiation dosage measuring device; and a shield portion surrounding the housing portion and including at least a member made of a specific material capable of blocking neutron radiation. The present invention was then completed. That is, the present invention can provide the followings.

(1) A first embodiment of the present invention is a dosimeter container including: a housing portion for housing a radiation dosage measuring device for measuring a dosage of predetermined radiation other than neutron radiation; and a shield portion surrounding the housing portion and including at least a LiF sintered body, the LiF sintered body transmitting the predetermined radiation to be measured with the radiation dosage measuring device, but blocking neutron radiation.

(2) A second embodiment of the present invention is the dosimeter container according to the first embodiment, in which the LiF sintered body is a $^6$LiF sintered body.

(3) A third embodiment of the present invention is the dosimeter container according to the second embodiment, in which the $^6$LiF sintered body includes $^6$LiF, and has a relative density of 83% or more to 90% or less, and has a good appearance with the occurrence of cracks and/or blisters being reduced on an outer surface.

(4) A fourth embodiment of the present invention is the dosimeter container according to any one of the first to third embodiments, in which the predetermined radiation is gamma radiation.

(5) A fifth embodiment of the present invention is the dosimeter container according to any one of the first to fourth embodiments, in which the shield portion includes at least two or more shield portion components, and the adjacent shield portion components of the at least two or more shield portion components that have mutually abuttable structures.

(6) A sixth embodiment of the present invention is the dosimeter container according to the fifth embodiment, in which the adjacent shield portion components have mutually fittable structures.

(7) A seventh embodiment of the present invention is the dosimeter container according to the fifth or sixth embodiment, in which the housing portion has a size substantially the same as or larger than the size of the radiation dosage measuring device, and the housing portion extends over the entirety of the shield portion components.

(8) An eighth embodiment of the present invention is the dosimeter container according to any one of the fifth to seventh embodiments, in which a shortest distance from an inner surface of the housing portion to outer surfaces of the shield portion components is constant.

(9) A ninth embodiment of the present invention is a dosage measuring body comprising the radiation dosage measuring device housed in the housing portion of the dosimeter container according to any one of the first to eighth embodiments.

Effects of the Invention

The present invention can provide a dosimeter container which contributes to both an improvement in measurement accuracy of a radiation dosage and a downsizing of a measuring apparatus.

PREFERRED MODE FOR CARRYING OUT THE INVENTION

Figure 1A:
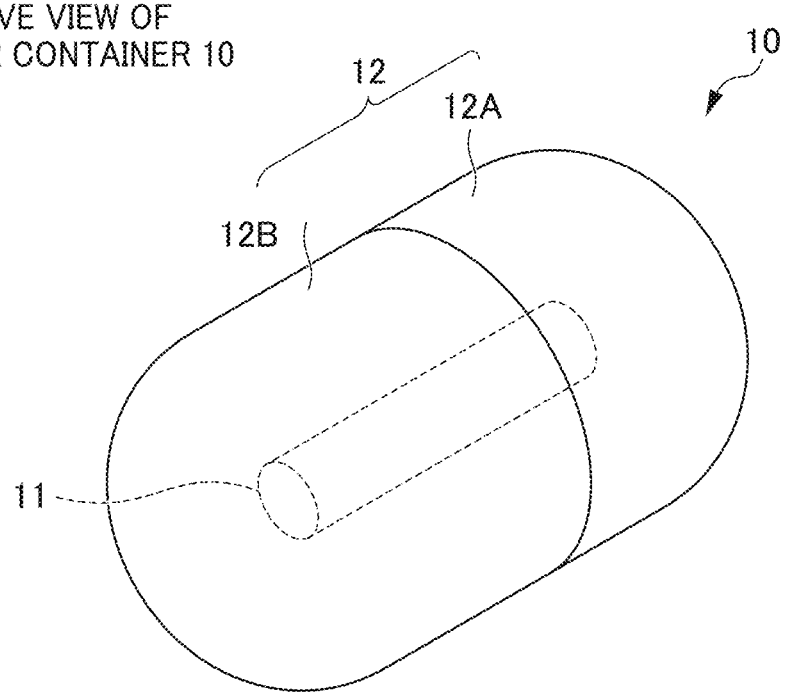
FIG. 1A shows a perspective view of a dosimeter container according to the first embodiment of the present invention.
Figure 1B:
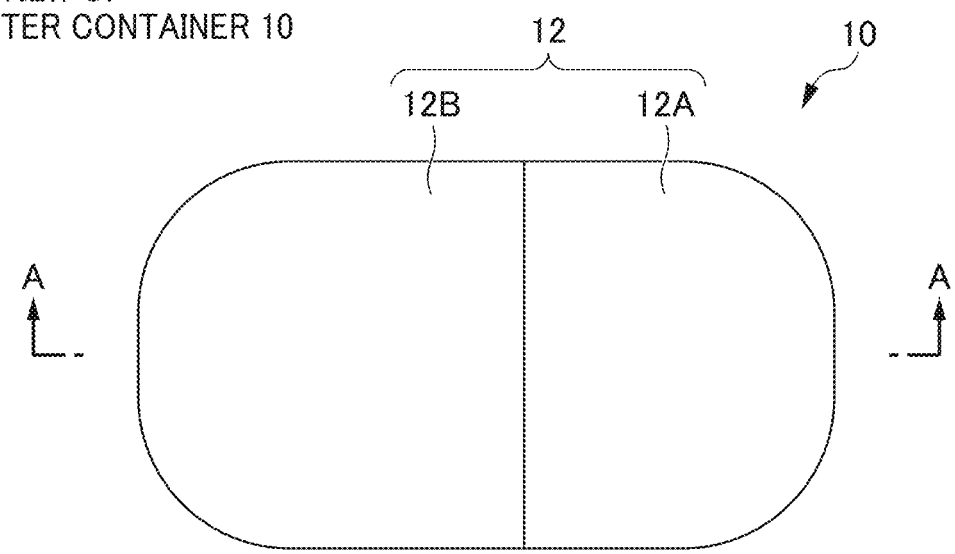
FIG. 1B shows a front view of the above dosimeter container.

Below, the specific embodiments of the dosimeter container according to the present invention will be described in detail, but the present invention shall not be limited to the following embodiments in any sense. Modifications may be appropriately made without departing from the spirit and scope of the present invention.

1. First Embodiment

<Dosimeter Container 10>

FIG. 1 schematically shows an example of a dosimeter container 10 according to the first embodiment of the present invention. More specifically, FIG. 1A shows a perspective view of the dosimeter container 10. FIG. 1B shows a front view of the dosimeter container 10, and FIG. 1C shows a cross-sectional view at the A-A section of FIG. 1B. FIG. 1D shows a perspective view of a body portion 12A of the dosimeter container 10, and FIG. 1E shows a perspective view of a lid portion 12B of the dosimeter container 10. Further, FIG. 1F schematically shows a state where a radiation dosage measuring device 51 is housed in a housing portion 11 of the dosimeter container 10.

The dosimeter container 10 according to the present embodiment includes the housing portion 11 for housing a radiation dosage measuring device and a shield portion 12 surrounding the housing portion 11.

[Housing Portion 11]

The housing portion 11 has a space for storing the radiation dosage measuring device.

The radiation dosage measuring device is an element which measures a dosage of predetermined radiation other than neutron radiation. The predetermined radiation may be selected from any type of radiation other than neutron radiation. However, the predetermined radiation is preferably gamma radiation in the view of an application to Boron Neutron Capture Therapy (BNCT). It is noted that the term "radiation dosage measuring device" as used herein shall encompass dosimeters in various forms, including a fluorescent glass element itself of a glass dosimeter, a fluorescent glass element of a glass dosimeter contained in a resin holder, and the like.

There is no particular limitation on the type of the element. Examples of the element include a fluorescent glass element of a glass dosimeter, ferrous sulfate or ferrous ammonium sulfate used in a Fricke dosimeter, and the like.

There is no particular limitation on the size of the housing portion 11, but it is preferred to be substantially the same as the size of a radiation dosage measuring device in view of downsizing the dosimeter container 10.

For example, when the radiation dosage measuring device is a fluorescent glass element of a glass dosimeter, the housing portion 11 has a cylindrical shape with φ2.5 mm to 3 mm, and a length of 10 mm to 15 mm.

[Shield Portion 12]

The shield portion 12 surrounds the housing portion 11, and is configured so as to enable neutron radiation which reaches the dosimeter container 10 to be blocked.

The shield portion 12 includes a member made of a material which blocks neutron radiation, but transmits at least radiation to be measured with a radiation dosage measuring device housed in the housing portion 11. This configuration enables a single radiation dosage measuring device housed alone in the housing portion 11 of the dosimeter container 10 to accurately measure the target radiation even when no radiation dosage measuring device is provided outside of the dosimeter container 10. Therefore, procedures of calculating a radiation dosage of the target radiation can be simplified, and the dosimeter container 10 can be downsized.

A material of the shield portion 12 will be described in detail below.

There is no particular limitation on the lower limit of the size of the shield portion 12, provided that it is sized so as to be able to appropriately block neutron radiation which reaches the shield portion 12, but appropriately transmit radiation to be measured with a radiation dosage measuring device. For example, the shield portion 12 preferably has a thickness of 2 mm or more, more preferably 3 mm or more, around the housing portion 11.

There is no particular limitation on the upper limit of the size of the shield portion 12, but the shield portion 12 preferably has a thickness of 8 mm or less, more preferably 5 mm or less, around the housing portion 11, in view of obtaining a thinner and smaller dosimeter as compared with a conventional one.

Moreover, the shield portion 12 has at least two or more shield portion components. In the present embodiment, the shield portion 12 has a body portion 12A and a lid portion 12B as the two or more shield portion components.

Figure 1C:
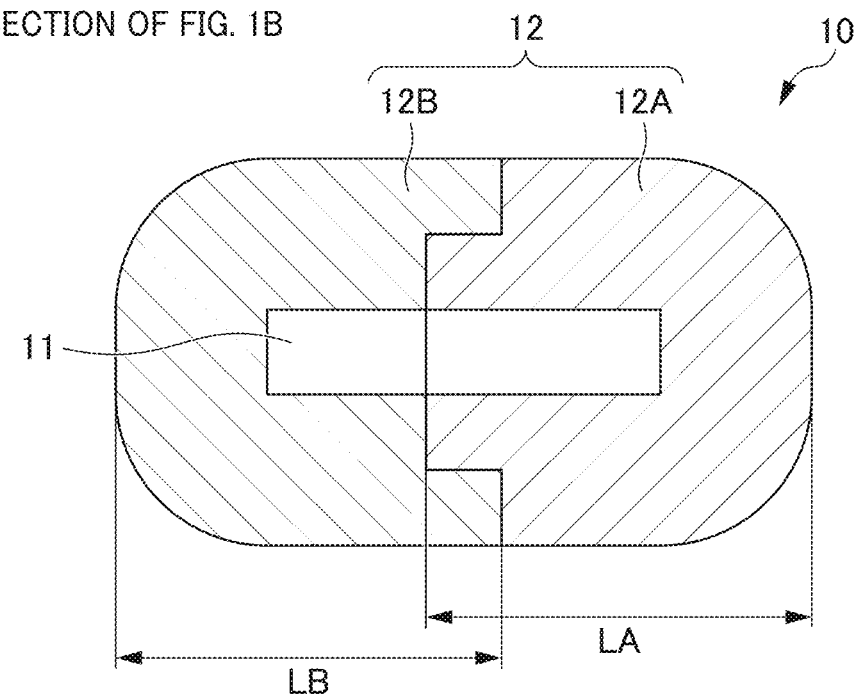
FIG. 1C shows a cross-sectional view at the A-A section of FIG. 1B.
Figure 1D:
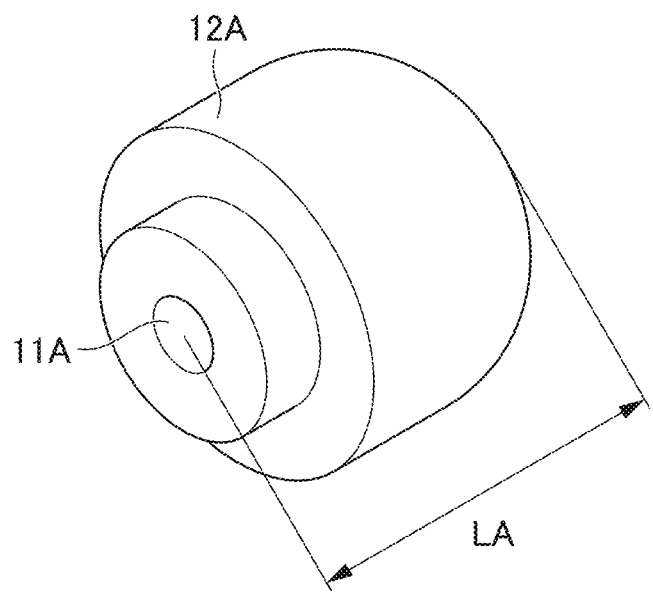
FIG. 1D shows a perspective view of a body portion of the above dosimeter container.
Figure 1E:
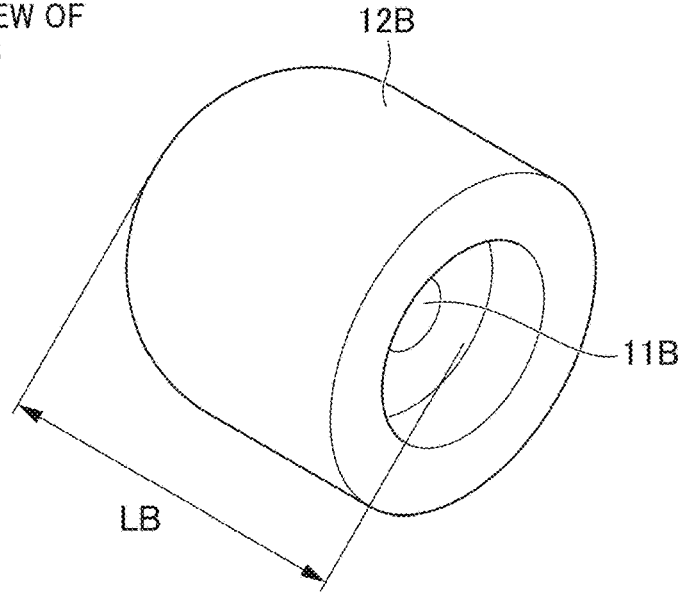
FIG. 1E shows a perspective view of a lid portion of the above dosimeter container.

As shown in FIGS. 1C, 1D, and 1E, the body portion 12A and the lid portion 12B, which are shield portion components adjacent to each other, have mutually abuttable structures.

The shield portion 12 includes two or more shield portion components, and adjacent shield portion components of the two or more shield portion components are configured to be able to abut to each other. This configuration enables easy mutual attachment and detachment of the shield portion components, which in turn enables a radiation dosage measuring device to be easily housed in and removed from the housing portion 11.

There is no particular limitation on the types of mutually abuttable structures. For Example, the body portion 12A and the lid portion 12B may be configured to have mutually fittable structures as shown in FIGS. 1C, 1D, and 1E. Alternatively, the body portion 12A and the lid portion 12B may be configured to be abutted to each other, and fixed with a fixing member at the outside of a joint region.

In particular, the body portion 12A and the lid portion 12B as adjacent shield portion components preferably have mutually fittable structures. When configured to have fittable structures, the body portion 12A and the lid portion 12B can be united together without fixing them with a fixing member at the outside of a joint region. Moreover, effects which may occur due to irradiation of the fixing member with neutron radiation and radiation other than neutron radiation can be disregarded.

There is no particular limitation on the types of fittable structures. For example, as shown in FIGS. 1C, 1D, and 1E, one shield portion component (the body portion 12A in this case) may be configured to have a protruded shape, and the other shield portion component (the lid portion 12B in this case) may be configured to have a depressed shape. Alternatively, one shield portion component may be an inclined member inclined in a predetermined direction, and the other shield portion component may be another inclined member having a shape symmetrical to the one shield portion component.

In particular, in view of suitably blocking neutron radiation with which the dosimeter container 10 is directly irradiated, and suitably transmitting the target radiation, the fittable structures are preferably configured such that one shield portion component (the body portion 12A in this case) has a protruded shape, and the other shield portion component (the lid portion 12B in this case) has a depressed shape, as shown in FIGS. 1C, 1D, and 1E.

Further, a length $L_A$ from the base of the body portion 12A to the apex portion of the protruded member is preferably the same as a length $L_B$ from the base of the lid portion 12B to the apex portion of the depressed member. When $L_A$ is the same as $L_B$, both the body portion 12A and the lid portion 12B can be obtained from a plate-like material having the same thickness, allowing for efficient manufacture of the dosimeter container 10 and reduced losses due to the cutting of raw materials.

As described above, the housing portion 11 preferably has a size substantially the same as that of a radiation dosage measuring device. In addition, the housing portion 11 preferably extends over the entirety of the shield portion components (the body portion 12A and the lid portion 12B in the present embodiment). When the housing portion 11 has a size substantially the same as that of a radiation dosage measuring device, and the housing portion 11 extends over the entirety of the shield portion components, the radiation dosage measuring device housed in the housing portion 11 itself can serve as a fixing member for fixing the shield portion components abutted together.

When the body portion 12A has a protruded shape, and the lid portion 12B has a depressed shape so that the body portion 12A can be fitted to the lid portion 12B, the length where the body portion 12A is protruded in a protruding manner and the depth where the lid portion 12B is depressed in a depressing manner may be appropriately selected in view of easy abutting and detachment of the body portion 12A and the lid portion 12B as well as in view of the fixing strength of the abutted shield portion components.

For example, when a radiation dosage measuring device is a fluorescent glass element of a glass dosimeter, the lower limit of the length where the body portion 12A is protruded in a protruding manner and the depth where the lid portion 12B is depressed in a depressing manner is preferably 1 mm or more, more preferably 1.5 mm or more, and even more preferably 2 mm or more. When the length where the body portion 12A is protruded in a protruding manner and the depth where the lid portion 12B is depressed in a depressing manner are too short, the lid portion 12B may detach from the body portion 12A during use of the dosimeter container 10 even when the body portion 12A is fitted to the lid portion 12B.

On the other hand, when a radiation dosage measuring device is a fluorescent glass element of a glass dosimeter, the upper limit of the length where the body portion 12A is protruded in a protruding manner and the depth where the lid portion 12B is depressed in a depressing manner is preferably 10 mm or less, more preferably 5 mm or less, and even more preferably 3 mm or less. When the length where the body portion 12A is protruded in a protruding manner and the depth where the lid portion 12B is depressed in a depressing manner are too long, loss of raw materials due to cutting may be significant, resulting in increased costs.

The shield portion components are each preferably configured to have a thickness so that the shortest distance from the inner surface of the housing portion to the outer surfaces of the shield portion components is constant. This configuration can allow a radiation dosage measuring device housed in the housing portion to be uniformly covered with the shield portion components, ensuring that neutron radiation from all directions can be blocked at an equal proportion. Therefore, a dosage measuring body can be placed according to a desired arrangement pattern in the container regardless of the irradiation directions of neutron radiation.

Figure 5:
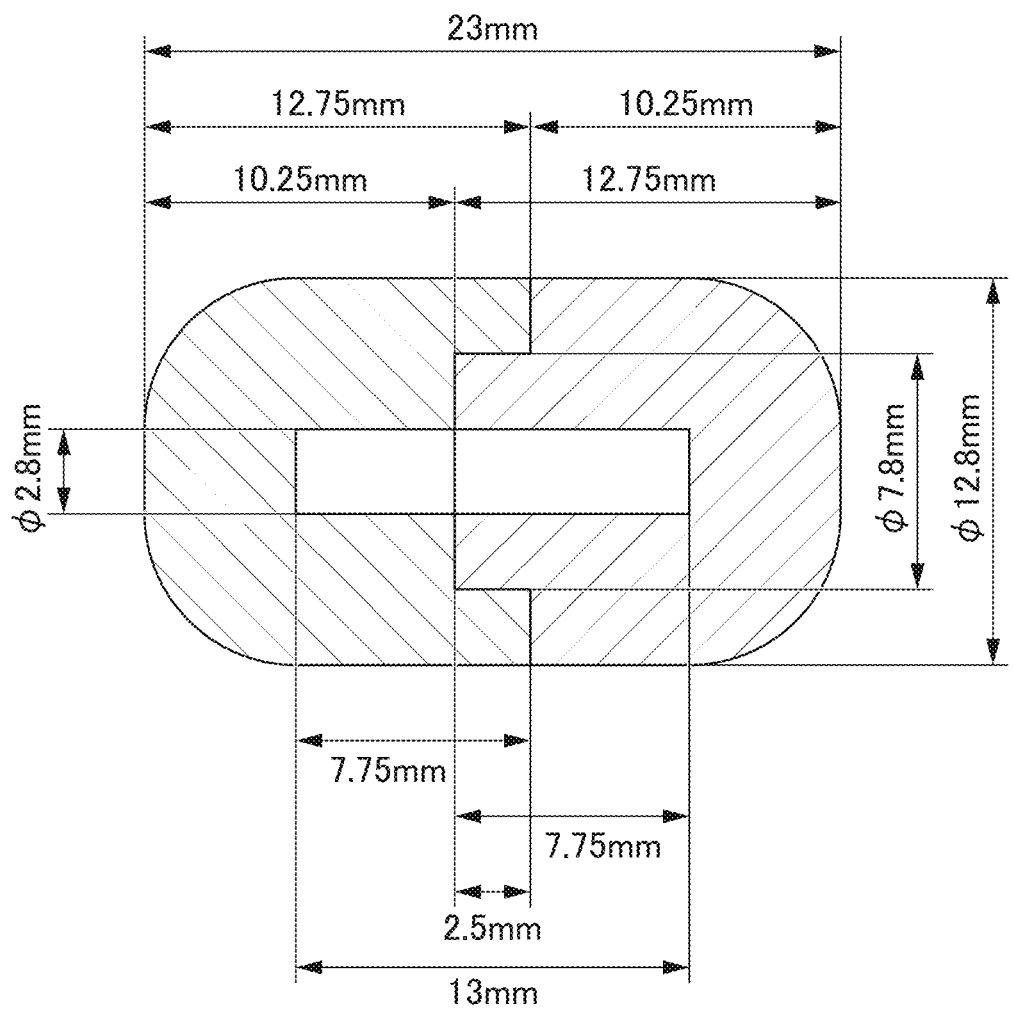
FIG. 5 shows the dimensions of a dosimeter container from the present Example as viewed in a cross-section from the front side.

For example, in a case where the thickness of the shield portion components is 5 mm as shown in FIG. 5, both end portions of the shield portion components may be curved with a radius of R5 as viewed in a cross-section at the corners of the end portions of the housing portion. This enables the shortest distance from the corners of the end portions of the housing portion to the outer surfaces of the shield portion components to be maintained equally at 5 mm. When the curvatures of R portions at the end portions of the shield portion components are appropriately designed according to the thicknesses of the shield portion components as described above, the shortest distance from the inner surface of the housing portion to the outer surfaces of the shield portion components can be configured to be constant.

Materials having the aforementioned properties include LiF-containing materials. Among these, a LiF sintered body is preferably used as a LiF-containing material because it has a high content of LiF with other ingredients that are unaffected by neutron radiation passing therethrough, and can contribute to obtaining a smaller and thinner dosimeter container 10.

It is worth noting that Li includes two stable isotopes, $^6$Li and $^7$Li, and their natural abundance percentages are 92.5 atom % and 7.5 atom % for $^7$Li and $^6$Li, respectively. Among these, $^6$Li contributes to blockage of neutron radiation, and thus the use of $^6$LiF in which $^6$Li is enriched can block neutron radiation at a higher efficiency. In view of the above, a $^6$LiF sintered body is more preferably used as the LiF sintered body. Below, a $^6$LiF sintered body will be described.

($^6$LiF Sintered Body)

(1) Ingredient: $^6$LiF

The $^6$LiF sintered body includes $^6$LiF as the main raw material, and has a higher neutron shielding performance as compared with other neutron moderators/shielding materials (for example, $CaF_2$, $MgF_2$, $MgF_2$—$CaF_2$ binary system, $MgF_2$—$CaF_2$—LiF ternary system, and the like). Moreover, the $^6$LiF sintered body includes $^6$LiF, but does not include other inorganic compounds as sintering aids or composite ingredients, and further is not a mixture with a thermoplastic resin and the like. Therefore, the $^6$LiF sintered body according to the present embodiment has a very high neutron shielding performance, and can contribute to obtaining a thinner and smaller shield portion 12.

The purity of $^6$Li in the $^6$LiF sintered body is preferably 95.0 atom or more, and the purity of LiF is preferably 99 wt % or more. If a large number of impurities such as metal ingredients (elements) are present in the $^6$LiF sintered body, these impurities may be radioactivated to emit gamma radiation when the $^6$LiF sintered body is irradiated with neutron radiation. $^6$LiF does not undergo radioactivation even when irradiated with neutron radiation. Therefore, the $^6$LiF sintered body according to the present embodiment having 95.0 atom % or more of $^6$Li and a LiF purity of 99 wt % has excellent neutron shielding performance, and in addition, advantageously reduces the effects of radiation exposure on the human body.

Further, $^6$LiF is prepared as a sintered body. Approaches to manufacturing a $^6$LiF sintered body include the single crystal growth method, a method involving solidifying from a melt, the sintering method, and the like.

However, the single crystal growth method requires precise control over a manufacturing process, and suffers from inferior quality stability, resulting in very expensive product prices. In addition, the resulting compact, which is a single crystal, has cleavability, resulting in problems such as susceptibility to cracking during processing.

Further, a method involving solidifying from a melt requires strict temperature control when cooling, and also requires a prolonged cooling time. Therefore, it is difficult to obtain a uniform and sound solidified material throughout the entirety of a relatively large size.

The ⁶LiF sintered body herein is obtained by the sintering method. Therefore, neutron shielding materials having high neutron shielding performance can be stably supplied.

(2) Relative Density

The ⁶LiF sintered body preferably has a relative density of 83% or more to 90% or less. As used in the present embodiment, the term "relative density" refers to a value obtained by dividing the density of a sintered body by the theoretical density (2.64 g/cm³) of LiF, and then multiplying the resulting value by 100.

A relative density of 83% or more to 90% or less means that the ⁶LiF sintered body is not highly densified. Advantageously, this leads to excellent cutting workability of the ⁶LiF sintered body.

A relative density that is too small may not be able to confer sufficient neutron shielding performance on the ⁶LiF sintered body. Further, a relative density that is too small may mean a higher cavity rate within the sintered body, resulting in inferior mechanical strength. This may cause breakage during processing and other problems.

On the other hand, a relative density that is too large results in a high degree of densification, and thus the residual stress inside the material may be released during processing of the sintered body even if sufficient neutron shielding ability is given to the ⁶LiF sintered body. This may generate a crack or the like.

(3) Thickness

There is no particular limitation on the thickness of the ⁶LiF sintered body as long as it is thick enough to suitably block neutron radiation. Specifically, the thickness of the ⁶LiF sintered body is preferably 2 mm or more, more preferably 3 mm or more.

There is no particular limitation on the upper limit of the thickness of the ⁶LiF sintered body, but the ⁶LiF sintered body is preferably thinner within a range where it can suitably block neutron radiation in view of obtaining a smaller and lighter shield portion 12. Specifically, the thickness of the ⁶LiF sintered body is preferably 8 mm or less, more preferably 5 mm or less.

(Method of Manufacturing ⁶LiF Sintered Body)

A method of manufacturing a ⁶LiF sintered body according to the present embodiment includes: a pressurizing step of pressurizing a ⁶LiF composition containing a ⁶LiF powder and an organic-based molding aid to obtain a pressed compact; and a firing step of firing the pressed compact at 630° C. or more to 830° C. or less. Further, the method may include a preliminary firing step of performing preliminary firing at 250° C. or more to 350° C. or less before the firing step.

<Dosage Measuring Body 1>

Figure 1F:
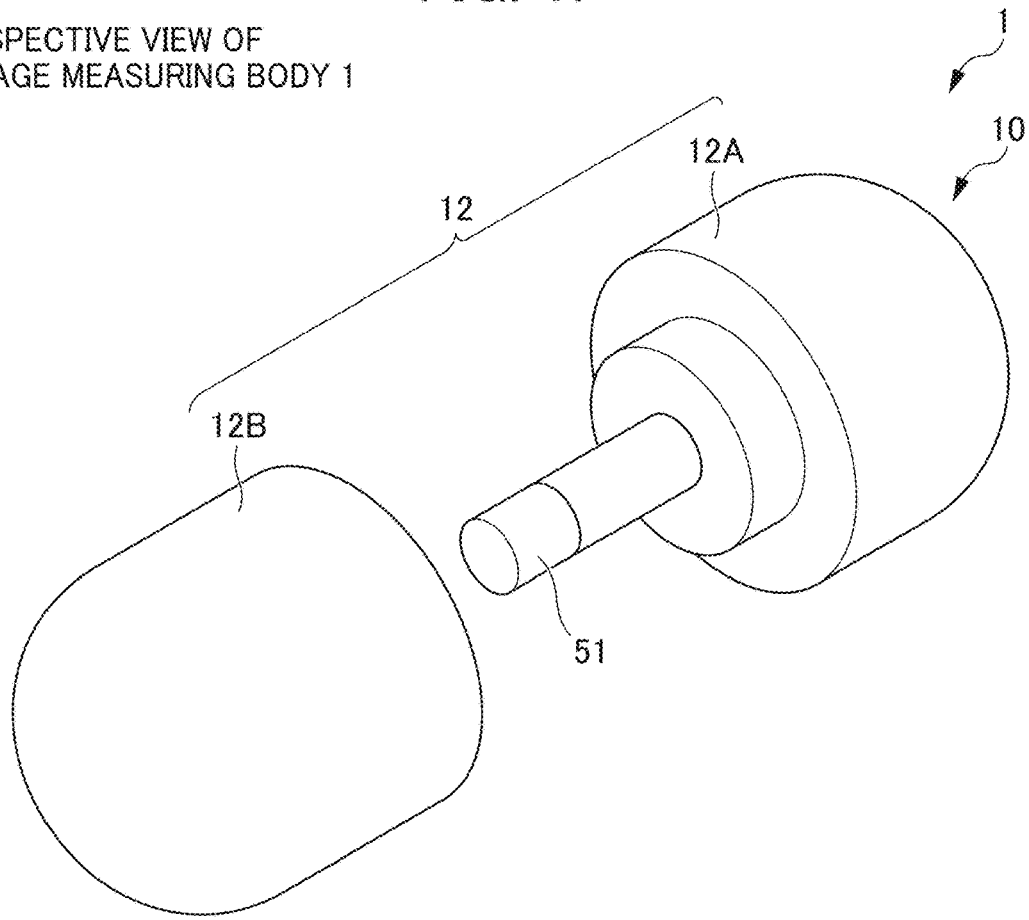
FIG. 1F shows a state where a radiation dosage measuring device is housed in a housing portion of the above dosimeter container.
Figure 2A:
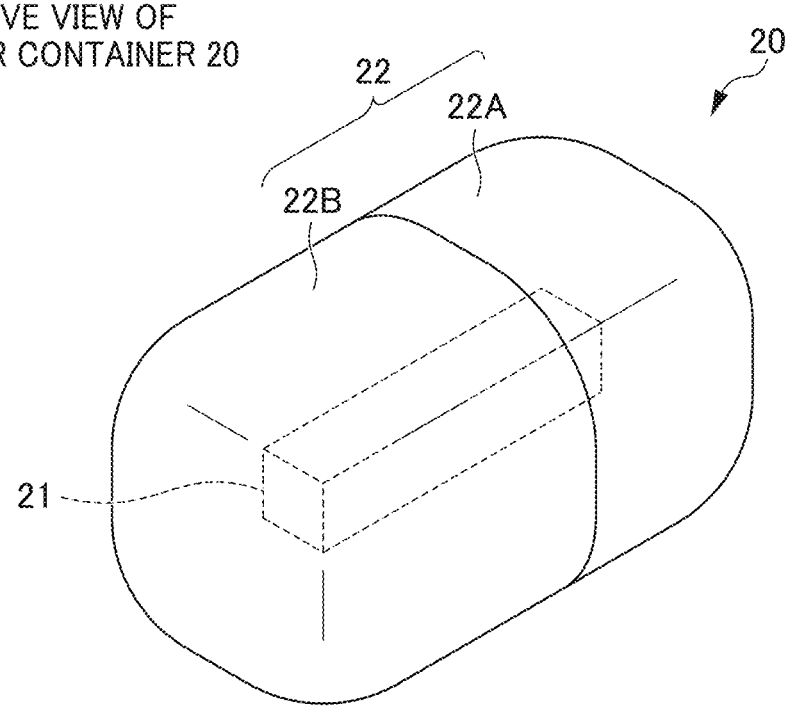
FIG. 2A shows a perspective view of a dosimeter container according to the second embodiment of the present invention.
Figure 2B:
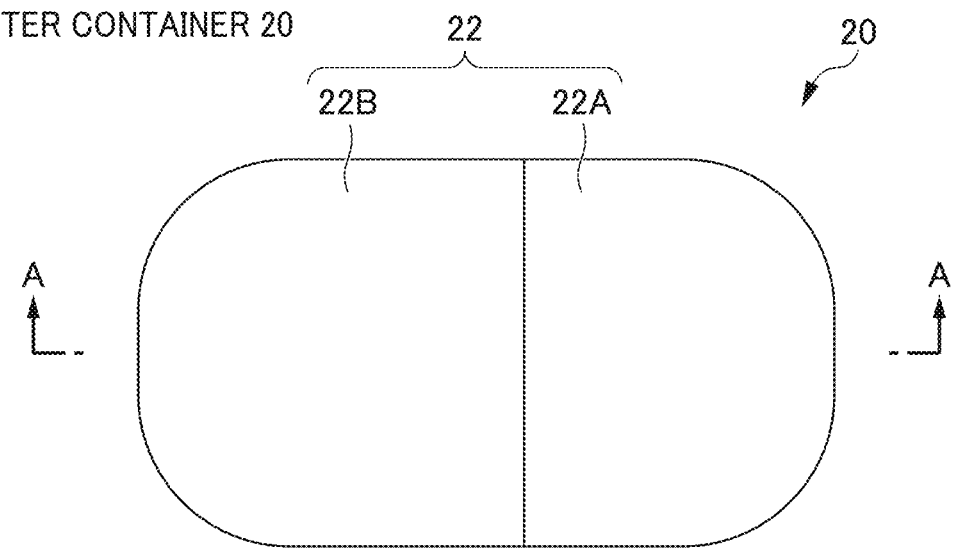
FIG. 2B shows a front view of the above dosimeter container.
Figure 2C:
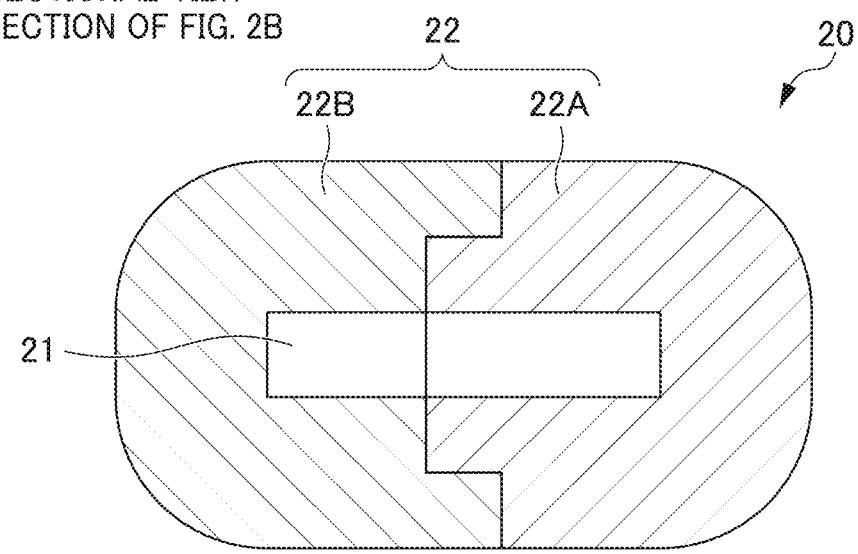
FIG. 2C shows a cross-sectional view at the A-A section of FIG. 2B.
Figure 2D:
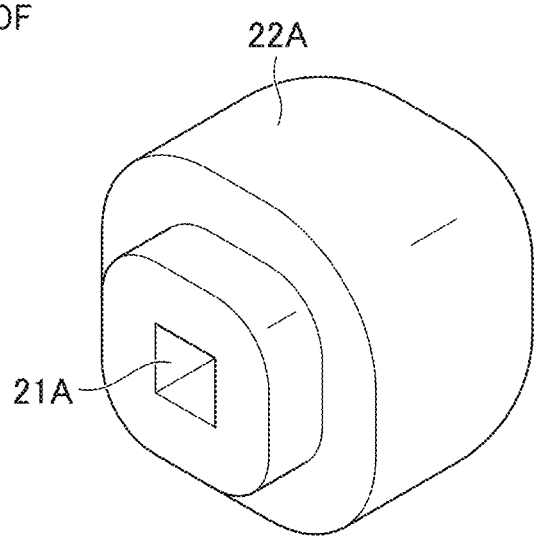
FIG. 2D shows a perspective view of a body portion of the above dosimeter container.
Figure 2E:
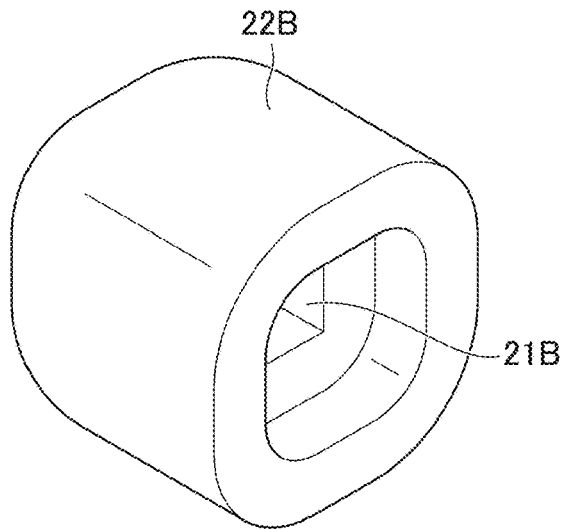
FIG. 2E shows a perspective view of a lid portion of the above dosimeter container.
Figure 2F:
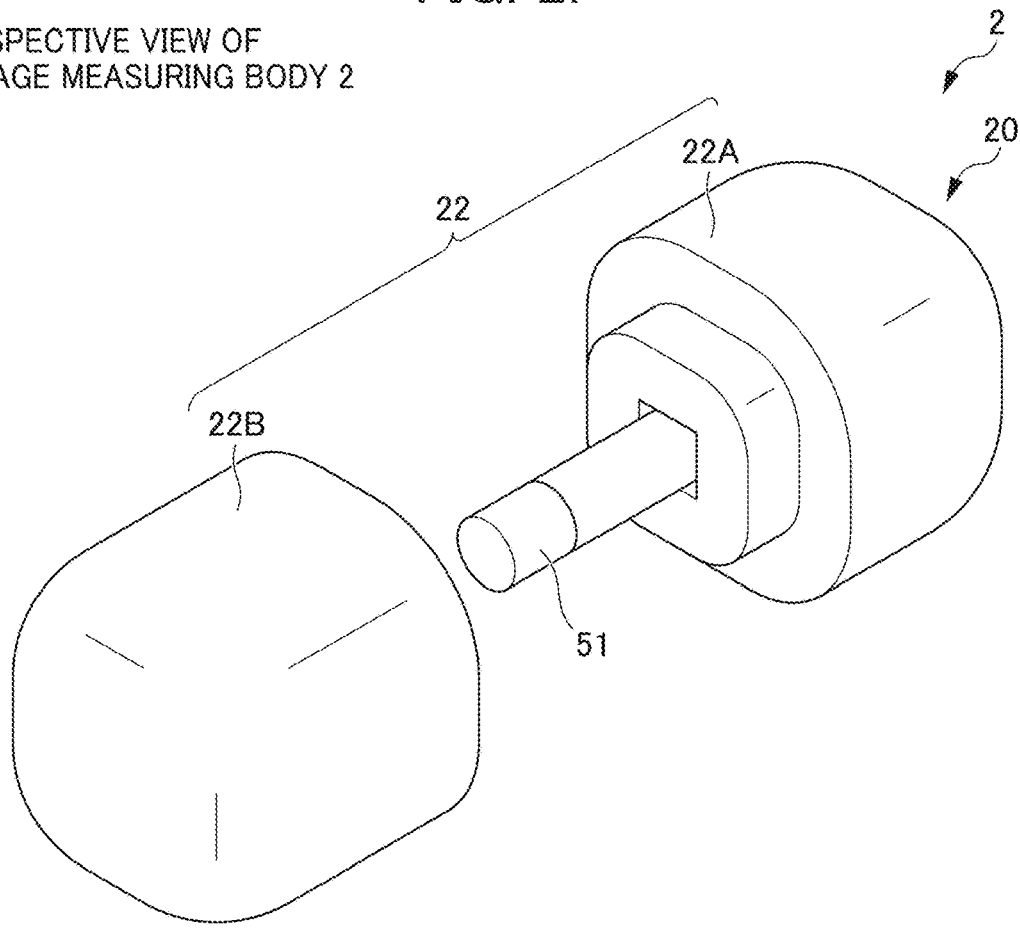
FIG. 2F shows a state where a radiation dosage measuring device is housed in a housing portion of the above dosimeter container.

FIG. 1F schematically shows an example of a dosage measuring body 1 according to the first embodiment of the present invention. For a dosage measuring body 1, the radiation dosage measuring device 51 is housed in the housing portion 11 of the dosimeter container 10.

According to the present embodiment, sufficient neutron shielding performance can be obtained even when the thickness of the dosimeter container 10 is thin. This enables the dosimeter container 10 to be designed to have a small size. Therefore, the dosimeter container 10 can be easily handled. For example, if the dosimeter container 10 is small, a plurality of dosimeter containers 10 may be arranged at a neutron radiation irradiation area in a measurement site so as to detect the presence of and/or difference in the strength of gamma radiation at the neutron radiation irradiation area (or by fewer measuring steps).

Further, the shield portion 12 as a component of the dosimeter container 10 includes a member made of a material which blocks neutron radiation but transmits at least radiation to be measured with a radiation dosage measuring device housed in the housing portion 11. This enables the radiation dosage measuring device housed in the housing portion 11 to accurately measure the target radiation. Therefore, procedures of calculating a radiation dosage of the target radiation can be simplified, contributing to the downsizing of the dosimeter container 10.

2. Second Embodiment

FIG. 2 schematically shows an example of a dosimeter container 20 according to the second embodiment of the present invention. More specifically, FIG. 2A shows a perspective view of the dosimeter container 10. FIG. 2B shows a front view of the dosimeter container 20, and FIG. 2C shows a cross-sectional view at the A-A section of FIG. 2B. FIG. 2D shows a perspective view of a body portion 22A of the dosimeter container 20, and FIG. 2E shows a perspective view of a lid portion 22B of the dosimeter container 20. Further, FIG. 2F schematically shows an example of a dosage measuring body 2 according to the second embodiment of the present invention, in which the radiation dosage measuring device 51 is housed in a housing portion 21 of the dosimeter container 20.

The dosimeter container 20 includes the housing portion 21 and a shield portion 22. The housing portion 21 is a member for storing a radiation dosage measuring device for measuring a dosage of predetermined radiation other than neutron radiation, and has similar functions as the housing portion 11 unless otherwise stated. The shield portion 22 is a member surrounding the housing portion 21, and has similar functions as the shield portion 12 unless otherwise stated.

The second embodiment differs from the first embodiment in the following points. In the first embodiment, the dosimeter container 10 has a capsule-like overall shape in which both end portions having hemispherical shapes are provided at both ends of a cylindrically shaped peripheral wall. In contrast, in the second embodiment, the dosimeter container 20 basically has a quadrangular prism-like overall shape with rounded corners.

Further, in the first embodiment, the housing portion 21 has a cylindrical shape which corresponds to the shape of the radiation dosage measuring device 51 (for example, a fluorescent glass element). In contrast, in the second embodiment, the housing portion 21 has a quadrangular prism-like shape in which the length of a side of the base of the housing portion 21 coincides with the length of the outer diameter of the base of the radiation dosage measuring device 51, and the height of the housing portion 21 is substantially the same as that of the radiation dosage measuring device 51.

As described above, there is no particular limitation on the shape of the dosimeter container, and it can be selected in an appropriate manner.

3. Third Embodiment

FIG. 3 schematically shows an example of a dosimeter container 30 according to the third embodiment of the present invention. More specifically, FIG. 3A shows a perspective view of the dosimeter container 30, and FIG. 3B shows a front view of the dosimeter container 30. FIG. 3C shows a top view of the dosimeter container 30, and FIG. 3D shows a cross-sectional view at the A-A section of FIG. 3C.

Figure 3A:
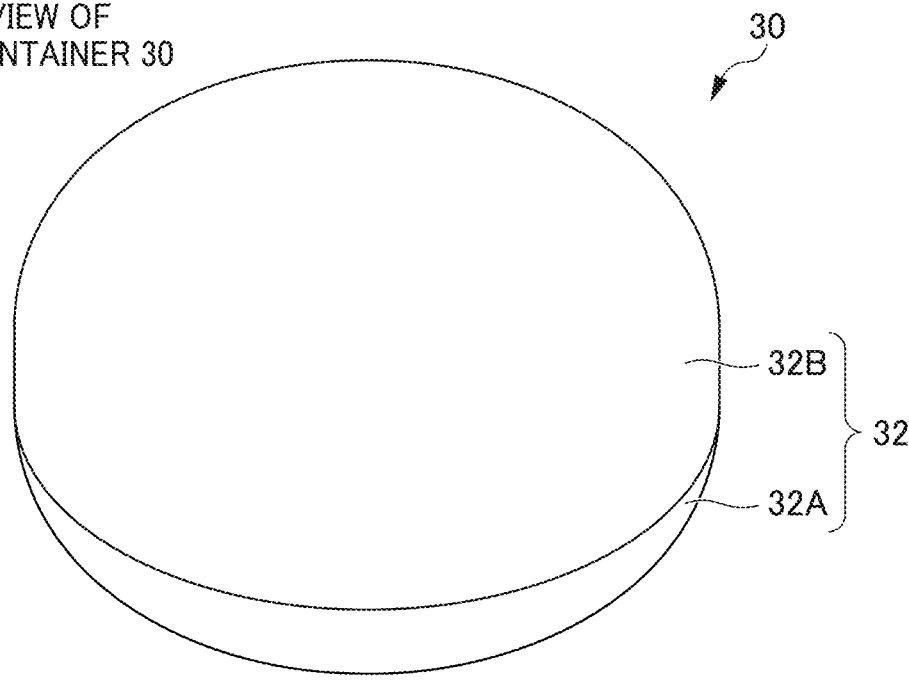
FIG. 3A shows a perspective view of a dosimeter container according to the third embodiment of the present invention.
Figure 3B:
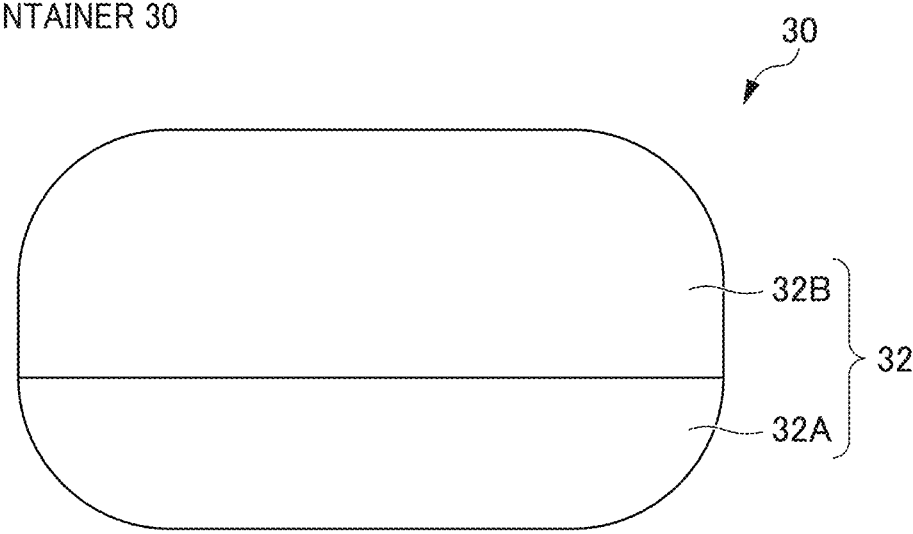
FIG. 3B shows a front view of the above dosimeter container.
Figure 3C:
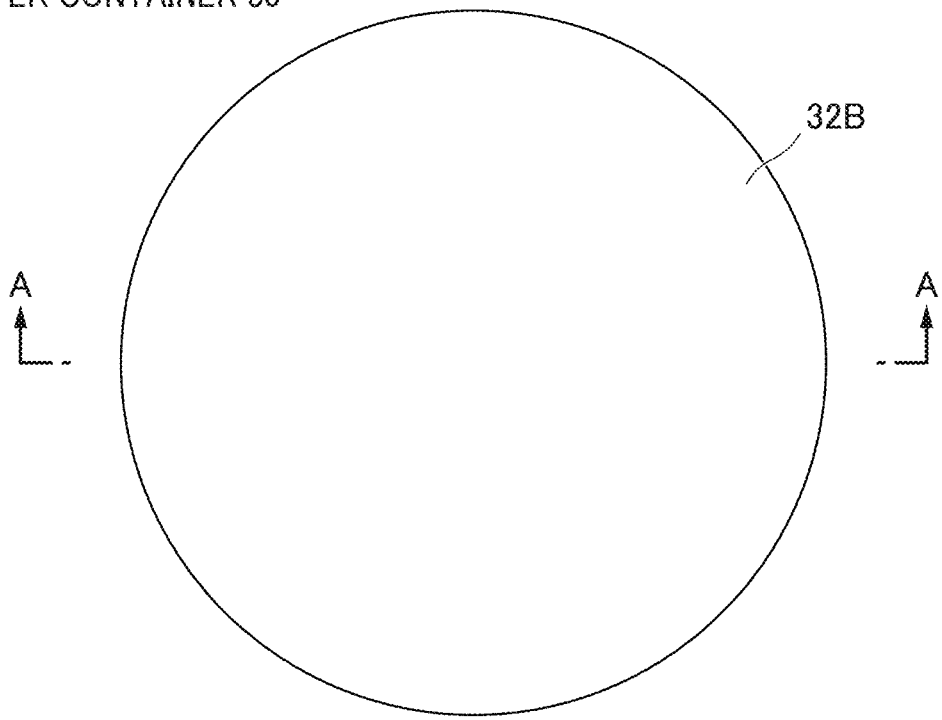
FIG. 3C shows a top view of the above dosimeter container.
Figure 3D:
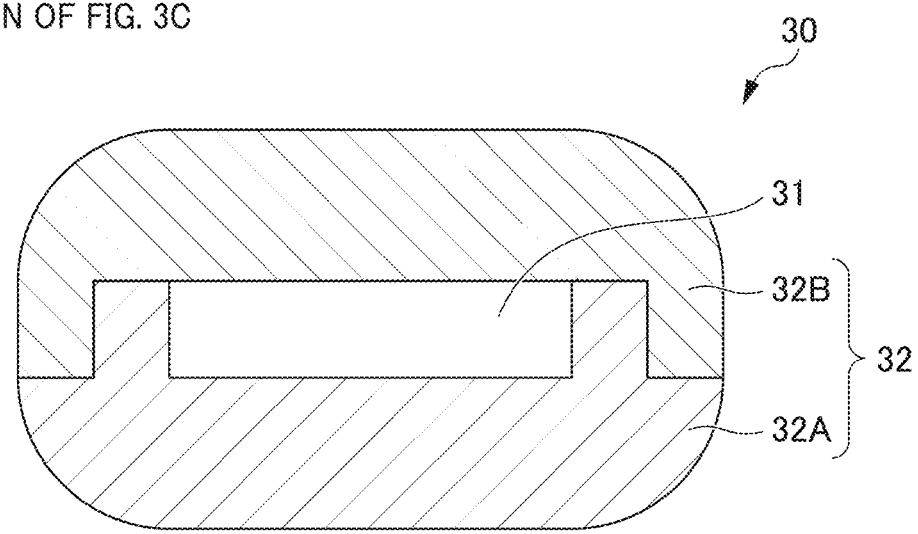
FIG. 3D shows a cross-sectional view at the A-A section of FIG. 3C.
Figure 3E:
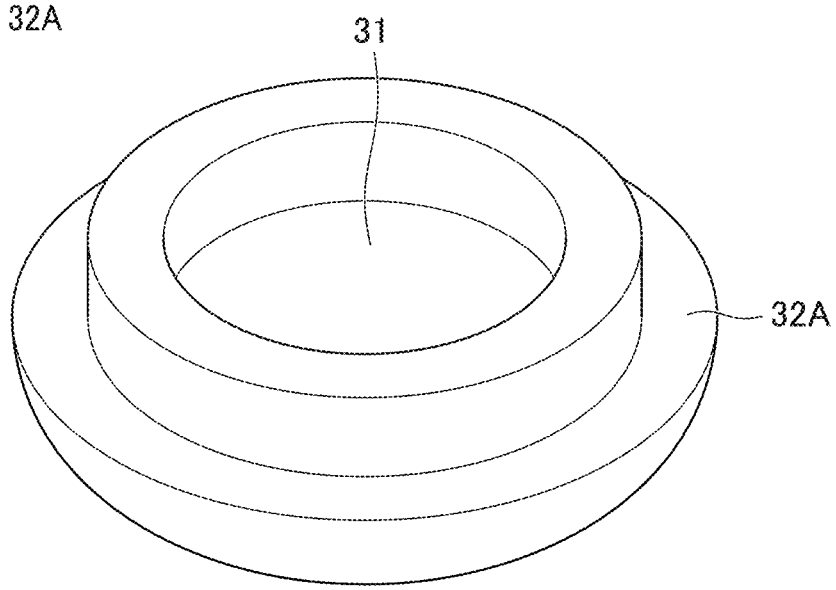
FIG. 3E shows a perspective view of a body portion of the above dosimeter container.
Figure 3F:
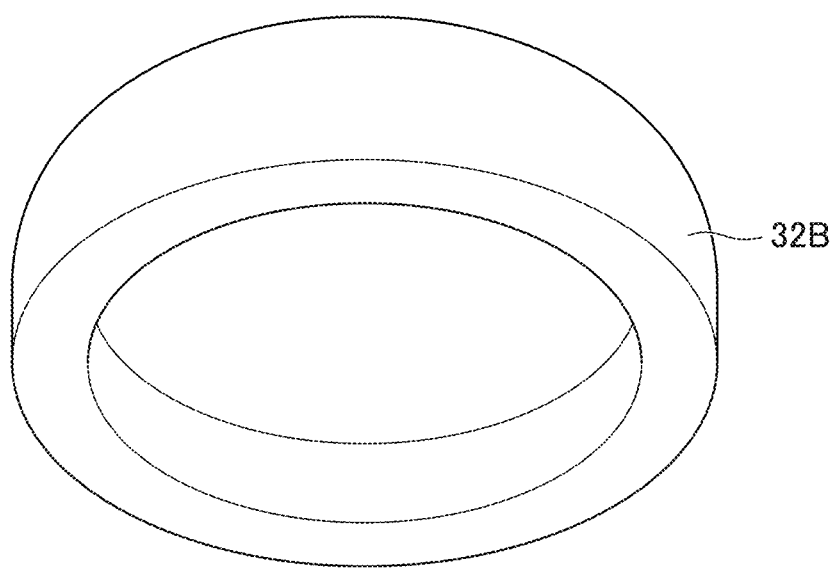
FIG. 3F shows a perspective view of a lid portion of the above dosimeter container.
Figure 3G:
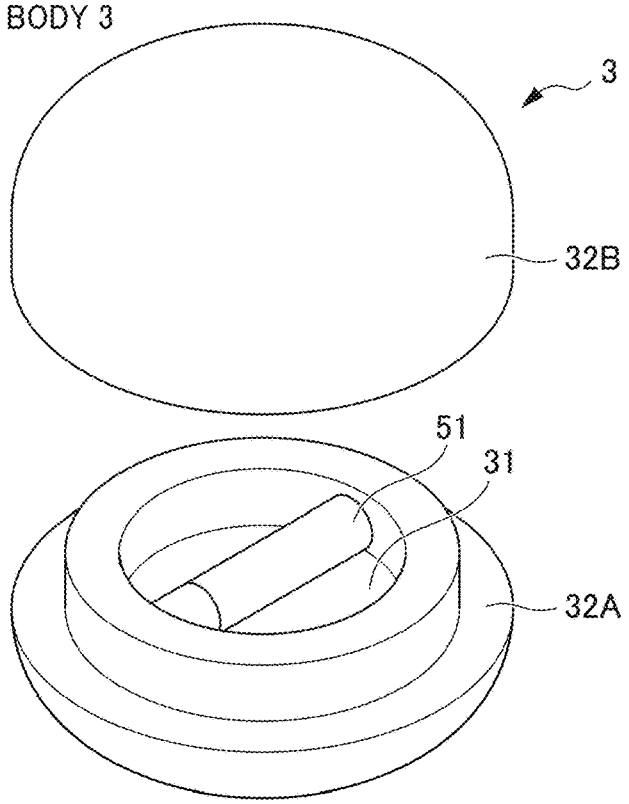
FIG. 3G shows a state where a radiation dosage measuring device is housed in a housing portion of the above dosimeter container.
Figure 4A:
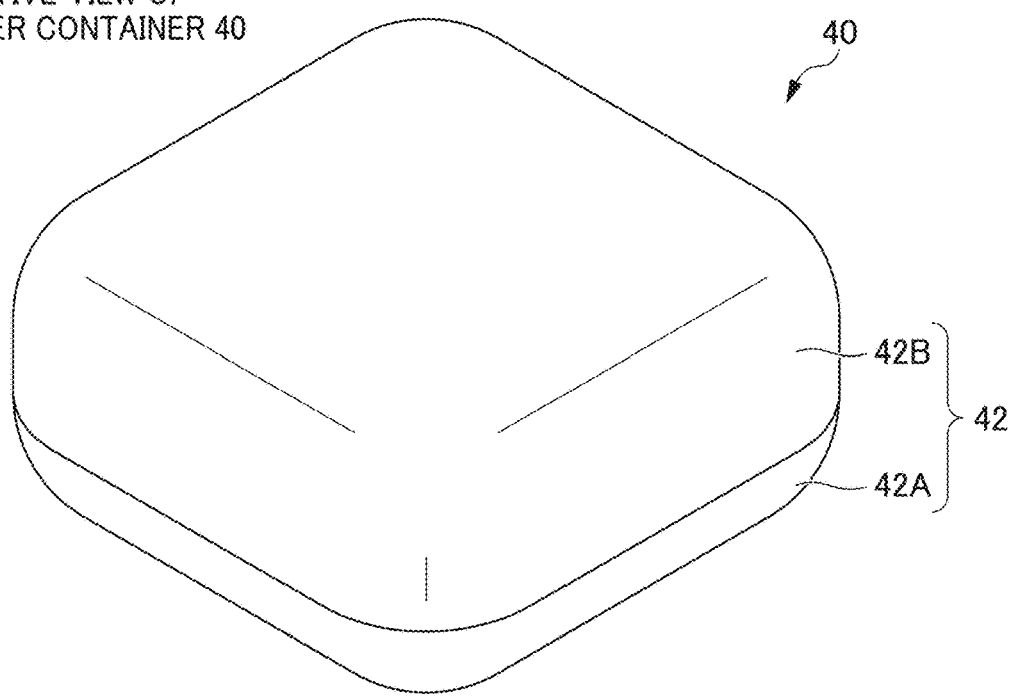
FIG. 4A shows a perspective view of a dosimeter container according to the fourth embodiment of the present invention.
Figure 4B:
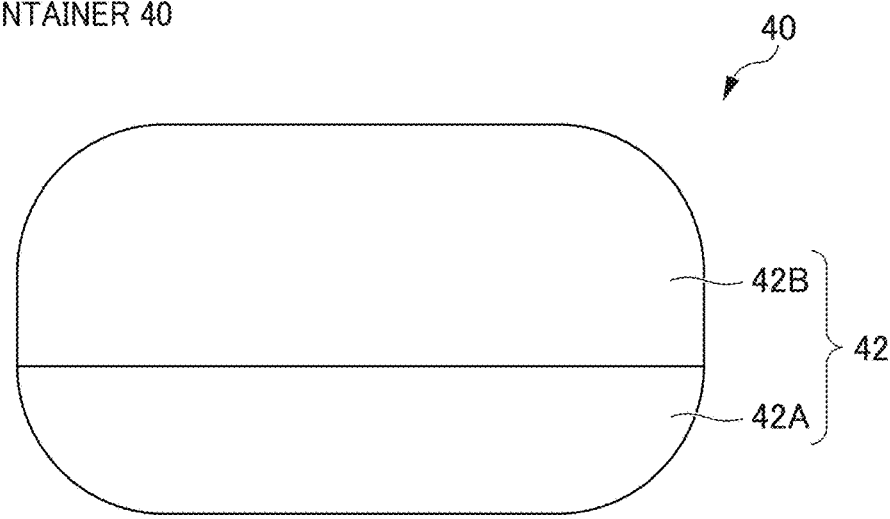
FIG. 4B shows a front view of the above dosimeter container.
Figure 4C:
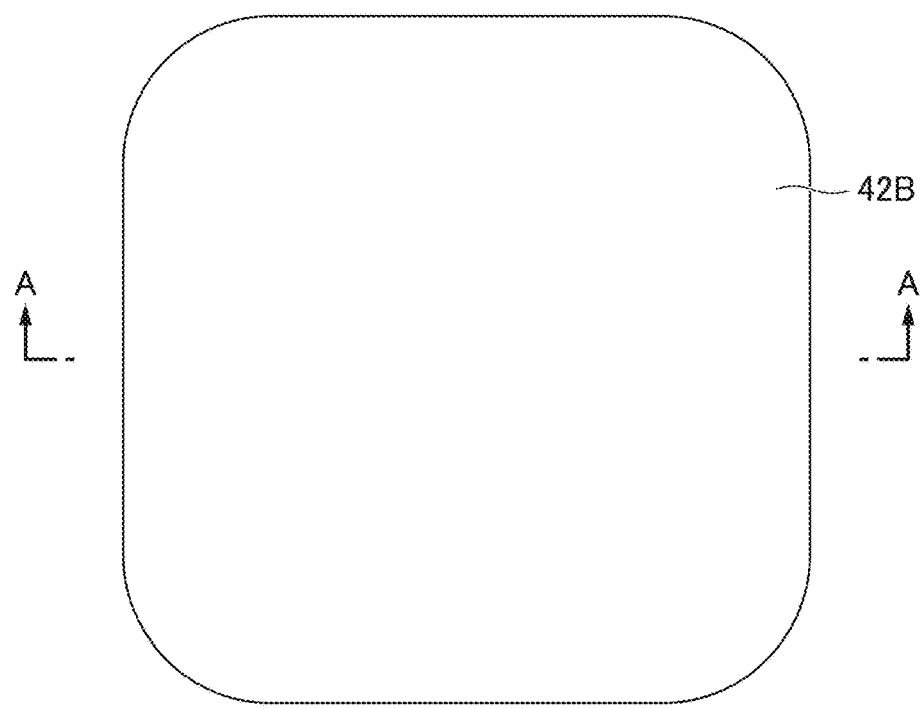
FIG. 4C shows a top view of the above dosimeter container.
Figure 4D:
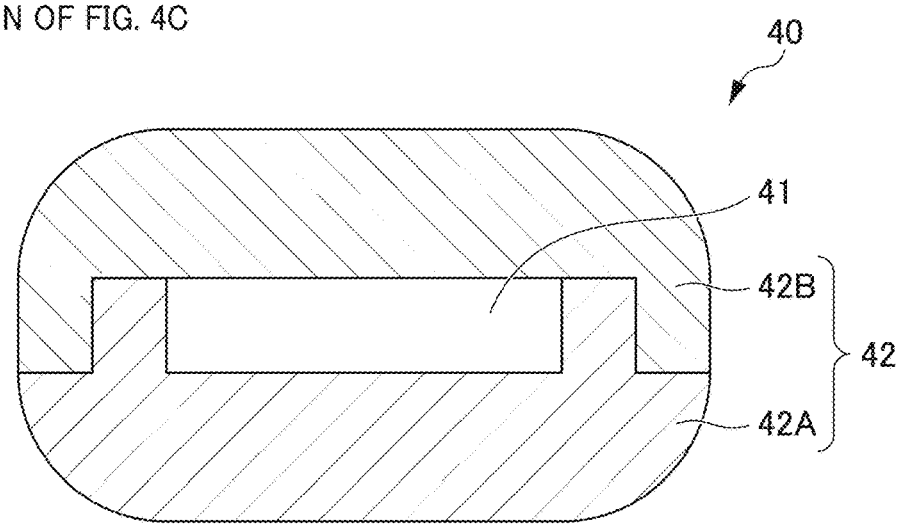
FIG. 4D shows a cross-sectional view at the A-A section of FIG. 4C.
Figure 4E:
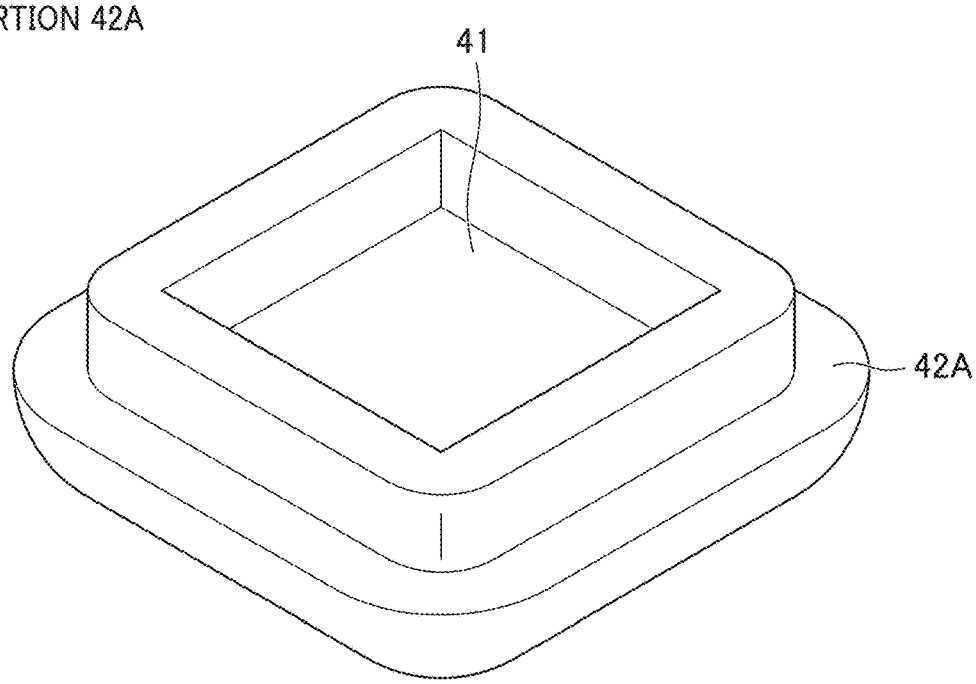
FIG. 4E shows a perspective view of a body portion of the above dosimeter container.
Figure 4F:
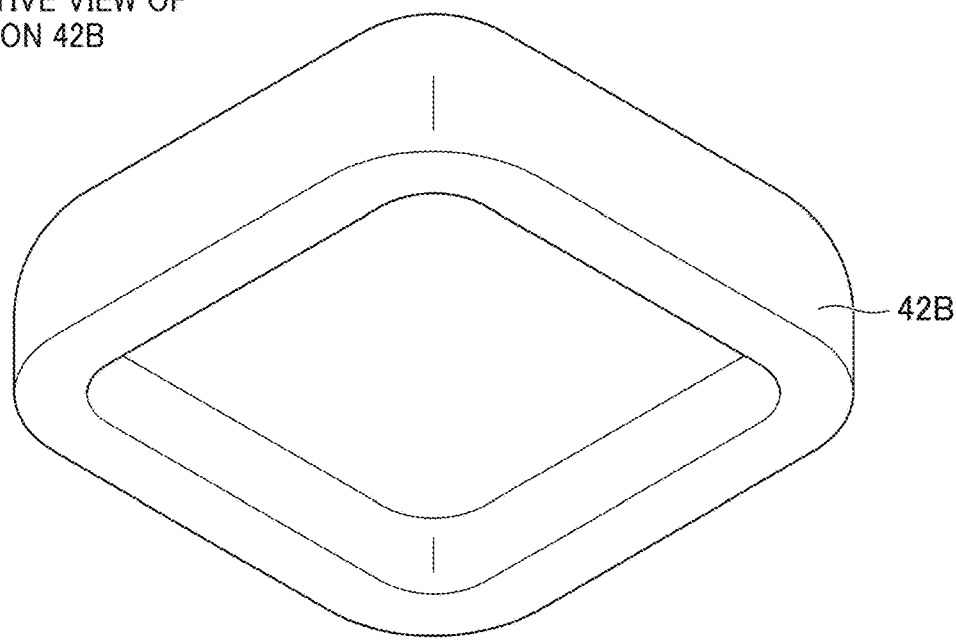
FIG. 4F shows a perspective view of a lid portion of the above dosimeter container.
Figure 4G:
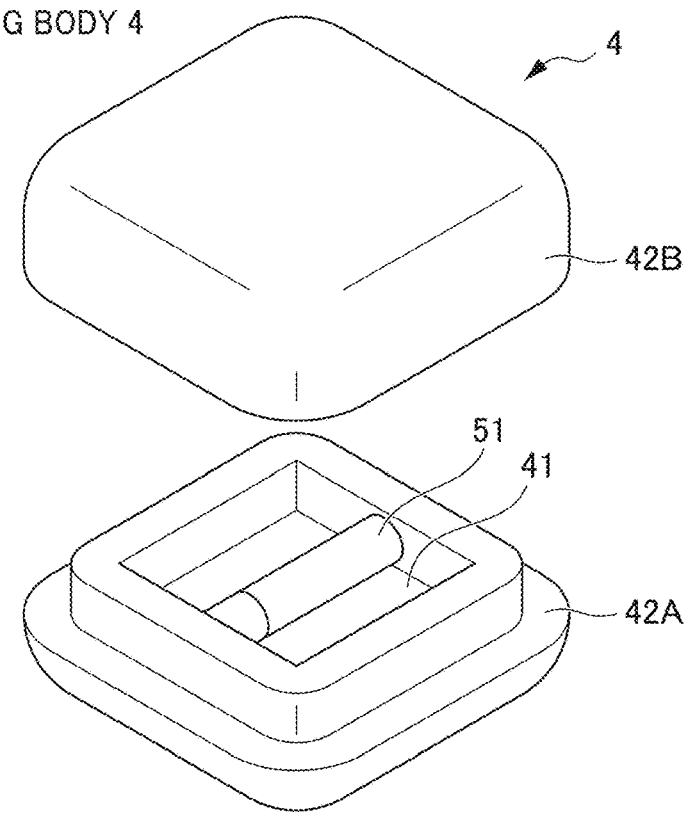
FIG. 4G shows a state where a radiation dosage measuring device is housed in a housing portion of the above dosimeter container.

FIG. 3E shows a perspective view of a body portion 32A of the dosimeter container 30, and FIG. 3F shows a perspective view of a lid portion 32B of the dosimeter container 30. Further, FIG. 3G schematically shows an example of a dosage measuring body 3 according to the third embodiment of the present invention, in which the radiation dosage measuring device 51 is housed in a housing portion 31 of the dosimeter container 30.

The dosimeter container 30 includes the housing portion 31 and a shield portion 32. The housing portion 31 is a member for storing a radiation dosage measuring device for measuring a dosage of predetermined radiation other than neutron radiation, and has similar functions as the housing portion 11 unless otherwise stated. The shield portion 32 is a member surrounding the housing portion 31, and has similar functions as the shield portion 12 unless otherwise stated.

The third embodiment differs from the first embodiment in the following points. The dosimeter container 10 has a capsule-like overall shape as described above in the first embodiment, while the dosimeter container 30 has a circular plate-like shape in the third embodiment.

Further, in the first embodiment, the housing portion 21 has a cylindrical shape which corresponds to the shape of the radiation dosage measuring device 51 (for example, a fluorescent glass element). In contrast, in the third embodiment, the housing portion 31 has a circular plate-like shape having an inner diameter substantially the same as the length of the radiation dosage measuring device 51 in the longitudinal direction.

Moreover, the housing portion 11 extends over the entirety of a shield portion component (the body portion 12A and the lid portion 12B in the present embodiment) while the housing portion 31 is provided only in the body portion 32A and not in the lid portion 32B in the third embodiment.

As described above, there is no particular limitation on the shape of the dosimeter container, and it can be selected in an appropriate manner. In particular, the housing portion preferably extends over the entirety of the shield portion component as in the first embodiment considering that the shield portion component can serve as a fixing member when the body portion is fitted to the lid portion.

4. Fourth Embodiment

FIG. 4 schematically shows an example of a dosimeter container 40 according to the fourth embodiment of the present invention. More specifically, FIG. 4A shows a perspective view of the dosimeter container 40, and FIG. 4B shows a front view of the dosimeter container 40. FIG. 4C shows a top view of the dosimeter container 40, and FIG. 4D shows a cross-sectional view at the A-A section of FIG. 4C. FIG. 4E shows a perspective view of a body portion 42A of the dosimeter container 40, and FIG. 4F shows a perspective view of a lid portion 42B of the dosimeter container 40. Further, FIG. 4G schematically shows an example of a dosage measuring body 4 according to the fourth embodiment of the present invention, in which the radiation dosage measuring device 51 is housed in a housing portion 41 of the dosimeter container 40.

The dosimeter container 40 includes the housing portion 41 and a shield portion 42. The housing portion 41 is a member for storing a radiation dosage measuring device for measuring a dosage of predetermined radiation other than neutron radiation, and has similar functions as the housing portion 11 unless otherwise stated. The shield portion 42 is a member surrounding the housing portion 41, and has similar functions as the shield portion 42 unless otherwise stated.

The fourth embodiment differs from the third embodiment as follows. The dosimeter container 30 has a circular plate-like overall shape in the third embodiment while the dosimeter container 40 has a substantively square plate-like shape in the fourth embodiment.

As described above, there is no particular limitation on the shape of the dosimeter container, and it can be selected in an appropriate manner.

EXAMPLES

Below, the present invention will be described in more detail with reference to an Example, but the present invention shall not be limited to the Example in any sense.
<Manufacture of Dosimeter Container 10>
A dosimeter container 10 was obtained via the following steps, has a similar shape as the dosimeter container 10 according to the first embodiment of the present invention, and has dimensions as shown in FIG. 5 at a cross-section as viewed from the front side (corresponding to FIG. 1C).
[Manufacture of $^6$LiF Sintered Body]
A cylindrical $^6$LiF sintered body having a height of about 16 mm was obtained via the following steps.
First, 100 mass parts of a $^6$LiF powder ($^6$Li purity: 95.0 atom % and LiF: 99%, Sigma-Aldrich) was mixed with 16 mass parts of a molding aid including stearic acid and cellulose to obtain a $^6$LiF composition.
(1) Pressurizing Step
Then, a mold with a diameter of 25 mm was filled with about 15.8 g of the $^6$LiF composition, and tapped to reduce voids where the $^6$LiF composition was not present.
Subsequently, the cylindrical mold was mounted on a hydraulic pressing machine, and pressed at 100 MPa to obtain a pressed compact.
(2) Preliminary Firing Step
The pressed compact was placed in a furnace under air atmosphere. The temperature was increased to 300° C. at 100° C./hr, and then the temperature was maintained for 5 hours to allow the majority of the molding aid included in the pressed compact to be decomposed or vaporized.
(3) Firing Step
After the preliminary firing step, the pressed compact was heated to 650° C. at 100° C./hr, and then the temperature was maintained for 5 hours. After that, cooling (air cooling) was performed to obtain a $^6$LiF sintered body.
[Processing of $^6$LiF Sintered Body]
Next, the $^6$LiF sintered body was cut circumferentially and internally and bored by machining processing so as to obtain dimensions in a cross-section as shown in FIG. 5. Then the dosimeter container 10 according to the Example was obtained.
<Evaluation>
[Evaluation of Pressed Compact]
The pressed compact obtained via the pressurizing step was found to have a relative density of 57.3% relative to $^6$LiF. Further, neither a blister nor a crack was observed when the appearance was visually inspected.
[Evaluation of $^6$LiF Sintered Body]
Further, the mass and relative density of the $^6$LiF sintered body obtained via the pressurizing step, the preliminary firing step, and the firing step were found to be 13.6 g and 86.2%, respectively. Moreover, neither a blister nor a crack was observed when the appearance was visually inspected. Furthermore, no internal defect such as a crack or a void was observed when a cut surface of the $^6$LiF sintered body cut with a precision cutting machine was visually inspected.

[Evaluation of Dosimeter Container 10]

A fluorescent glass element was housed in the housing portion 11 of the dosimeter container 10, and the shield portion 12 was irradiated with gamma radiation and neutron radiation from the outside of the dosimeter container 10. Results showed that the dosimeter container 10 had excellent neutron shielding ability while transmitting gamma radiation, demonstrating that the dosimeter container 10 is suitable for measuring gamma radiation.

EXPLANATION OF REFERENCE NUMERALS

1 Dosage measuring body according to the first embodiment
10 Dosimeter container according to the first embodiment
11 Housing portion
12 Shield Portion
12A Body portion
12B Lid portion
2 Dosage measuring body according to the second embodiment
20 Dosimeter container according to the second embodiment
3 Dosage measuring body according to the third embodiment
30 Dosimeter container according to the third embodiment
4 Dosage measuring body according to the fourth embodiment
40 Dosimeter container according to the fourth embodiment
51 Radiation dosage measuring device

What is claimed is:

1. A dosimeter container comprising: a housing portion for housing a radiation dosage measuring device for measuring a dosage of predetermined radiation other than neutron radiation; and a shield portion surrounding the housing portion and including at least a LiF sintered body, the LiF sintered body transmitting the predetermined radiation to be measured with the radiation dosage measuring device but blocking neutron radiation, wherein the LiF sintered body is a $^6$LiF sintered body including $^6$LiF and has a relative density of 83% or more to 90% or less which is obtained by dividing the density of the sintered body by a theoretical density equal to 2.64 g/cm$^3$ of LiF and multiplying the resulting value by 100.

2. The dosimeter container according to claim 1, wherein the predetermined radiation is gamma radiation.

3. The dosimeter container according to claim 1, wherein the shield portion includes at least two or more shield portion components, and adjacent shield portion components of the at least two or more shield portion components that have mutually abuttable structures.

4. The dosimeter container according to claim 3, wherein the adjacent shield portion components have mutually fittable structures.

5. The dosimeter container according to claim 4, wherein the housing portion has a size the same as or larger than the size of the radiation dosage measuring device, and
 the housing portion extends over the entirety of the shield portion components.

6. The dosimeter container according to claim 5, wherein a shortest distance from an inner surface of the housing portion to outer surfaces of the shield portion components is constant.

7. A dosage measuring body, comprising the radiation dosage measuring device housed in the housing portion of the dosimeter container according to claim 1.

* * * * *